United States Patent [19]
Hattori

[11] Patent Number: 5,989,258
[45] Date of Patent: Nov. 23, 1999

[54] APPARATUS FOR AND METHOD OF BONE DRILLING

[76] Inventor: Morihiro Hattori, 16-12, Douetsu 3-Chome, Shimada-shi, Shizuoka, 427, Japan

[21] Appl. No.: 08/931,279

[22] Filed: Sep. 16, 1997

[51] Int. Cl.⁶ .................................................. A61B 17/16
[52] U.S. Cl. .............................................. 606/80; 606/96
[58] Field of Search .................................. 606/96, 97, 98, 606/80, 79

[56] References Cited

U.S. PATENT DOCUMENTS

| | | | |
|---|---|---|---|
| 2,494,229 | 1/1950 | Collison | 606/96 |
| 4,119,092 | 10/1978 | Gil | 606/96 |
| 4,570,624 | 2/1986 | Wu | 606/96 |
| 5,405,348 | 4/1995 | Anspach, Jr. et al. | 606/96 |
| 5,569,254 | 10/1996 | Carlson et al. | 606/79 |

Primary Examiner—Michael Buiz
Assistant Examiner—David O. Reip
Attorney, Agent, or Firm—Whitman, Curtis & Whitham

[57] ABSTRACT

An apparatus for bone drilling comprising a support member with a guide hole having an aperture of predetermined diameter attached to the side of an object of drilling, and a drilling device having a rotative cutting implement (drill) to be rotated. A guide member is integrally or separately provided on the outer periphery of the rotative cutting implement (drill), and the diameter of the outer periphery of the guide member substantially corresponds to that of the guide hole.

13 Claims, 13 Drawing Sheets

APPARATUS FOR AND METHOD OF BONE DRILLING

BACKGROUND OF THE INVENTION

1. Field of the Invention

The present invention relates to an apparatus for bone drilling as well as a method of bone drilling which, for example during so-called "implantation" (of artificial tooth) treatment in dentistry, enables a dentist to accurately drill a hole for implantation, into which an implant is implanted, at a predetermined position in a jaw bone.

2. Description of the Related Art

There is a dental treatment called "implantation", which is adopted in order to fix an artificial tooth as a false tooth. During the implantation process, an implantation hole is drilled at a predetermined position in a jaw bone (the maxilla or the mandible), and an implant made of metal is implanted in the implantation hole. Then an artificial tooth is fixed thereon via various types of metal fittings.

However, the following exist with regard to the implantation treatment have been existing.

Firstly, an ordinary case, the implantation hole is specified in advance by means of computed tomography. Namely, the most appropriate position for the implantation hole is determined by checking the state of such a position for implantation in relation to the nerves or the other teeth through the computed tomography. When the position of the implantation hole is determined, the drilling is operated by a drilling apparatus in order to form a desirous implantation hole.

However, when the most appropriate position for implantation hole is specified through computing tomography, in some cases the deviation of drilling point may actually occur, which results in inaccurate positioning of formation of desirous implantation hole. This inaccurate positioning of drilling may occur due to play, for example, between a guide hole formed in a surgical stent and a drill which works as the rotative cutting implement (drill) on the side of drilling apparatus.

When the deviated implantation hole is formed, it becomes necessary to amend such an deviated position of the implantation hole, which is troublesome to the dentist, and requires a skilled operation which is time consuming to.

With regard to the above problem relating to the deviated positioning, a countermeasure that can be taken is the size (diameter) of the guide hole formed in the surgical stent is minimized so that the play between the drill and the guide hole may not be allowed. However, it should be noted regardless of the minimization of size to the guide hole, that there may be a case when the drilling operation along the guide hole of the above surgical stent may cause damage to the surgical stent. In addition, it should be noted that the shavings (shaved particles) of drilling may go inside the implantation hole, which eventually causes damage to the accurate implantation structure. Consequently, in addition to the above problem which exists before the minimization of the guide hole is made, if the minimization is further made in regard to the size of the guide hole, the problem as above discussed may become more remarkable and therefore worse.

There are in fact several types of guide apparatus provide to overcome the above problem, but all of these apparatuses require the skilled operation and the long operating time including further amendment after the drilling operation. Consequently, the efficiency of operation is not good.

SUMMARY OF THE INVENTION

It is an object of the present invention to provide an apparatus for bone drilling as well as a method of bone drilling which, for example during the "implantation" treatment in dentistry, enables a dentist to accurately drill a hole for implantation, into which an implant is implanted, at a predetermined position in a jaw bone.

To achieve the object mentioned above, according to the present invention, there is provided an apparatus for bone drilling, comprising a support member with a guide hole having a predetermined aperture diameter attached to the side of an object to be drilled, and a drilling device having a rotative cutting implement (drill) to be rotated. A guide member is integrally or separately provided on the outer periphery of the rotative cutting implement (drill), and the diameter of the outer periphery of the guide member substantially corresponds to that of the aperture of the guide hole.

Preferably, a guide ring is provided on the guide hole, so that the diameter of the outer periphery of the guide member of the drilling device may substantially correspond to that of the aperture of the guide ring.

Preferably, a plurality of water fillers may be formed on the guide member in order to introduce water inside the guide member.

Preferably, the top end of the guide member may obliquely be cut away so that water may be filled from the top end.

Further, according to the present invention, there is provided an apparatus for bone drilling, comprising a surgical stent attached to a position corresponding to implantation position and has at least one guide hole having a predetermined diameter of an aperture, and a drilling device having a rotative cutting implement (drill) to be rotated. A guide member is integrally or separately provided on the outer periphery of the rotative cutting implement (drill), and the diameter of the outer periphery of the guide member substantially corresponds to that of the aperture of the guide hole.

Preferably, a guide ring may be provided on the guide hole of the surgical stent so that the diameter of the outer periphery of the guide member of the drilling device may substantially correspond to that of the aperture of the guide ring.

Preferably, a plurality of water fillers may be formed on the guide member in order to introduce water inside the guide member.

Preferably, the top end of the guide member may obliquely be cut away so that water may be filled from the top end.

Further, according to the present invention, there is provided a method of bone drilling, comprising a step to attach a support member with a guide hole having a predetermined diameter of aperture to the side of an object of drilling, a step to prepare a drilling device having a rotative cutting implement (drill) to be rotated, in a state that a guide member is integrally or separately provided on the outer periphery of the rotative cutting implement (drill), and that a diameter of the outer periphery of the guide member substantially corresponds to that of the aperture of the guide hole, and a step to drill by the rotative cutting implement (drill) in a state that the guide member is inserted in the guide hole.

Preferably, there may also be a step to provide a guide ring having an aperture of predetermined diameter on the guide hole.

Further, according to the present invention, there is provided a method of bone drilling, comprising a step to attach a surgical stent with at least one guide hole having a predetermined diameter of an aperture to a position corresponding to implantation position, a step to prepare a drilling device having a rotative cutting implement (drill) to be rotated, in a state that a guide member is integrally or separately provided on the outer periphery of the rotative cutting implement (drill), and that a diameter of the outer periphery of the guide member substantially corresponds to that of the aperture of the guide hole, and a step to drill by the rotative cutting implement (drill) in a state that the guide member is inserted in the guide hole.

Preferably, there may also be a step to provide a guide ring having a predetermined diameter of aperture on the guide hole.

With this structure, a guide hole having a predetermined diameter of aperture has been provided in advance on the side of an object of treatment, so that a drilling operation may be made by rotating a rotative cutting implement (drill) such that a guide member, of which the diameter of the outer periphery substantially corresponds to that of the aperture of the guide hole, is inserted in the guide hole. Thus the "shaking" or "deviation" of the drilling apparatus may be inhibited, so that the accurate drilling and forming of the hole at the desirous position can be carried out.

With the addition of the guide hole and the guide member, it is possible to drill and form a predetermined hole accurately at the predetermined position, thus the efficiency of operation may improve.

There is a plurality of water fillers, and in addition, the top of the guide member is obliquely cut away, thus the high efficiency of water filling may be expected.

The length of the projecting drilling implement may uniformly be determined by setting the length of the guide member to any predetermined length, thus any predetermined depth of drilling may be obtained.

When the present invention is applied to "implantation" treatment in dentistry, the facile "implantation" treatment may be accomplished.

BRIEF DESCRIPTION OF THE DRAWINGS

The invention will be described below in detail with reference to the accompanying drawings, in which.

DETAILED DESCRIPTION OF THE INVENTION

An embodiment of the present invention will now be described with reference to FIGS. 1 through 13. The present embodiment relates to an example in which the present invention is applied to an "implantation" treatment in dentistry. The outline of the implantation treatment in dentistry will firstly be described with reference to FIG. 1.

Figure 1:
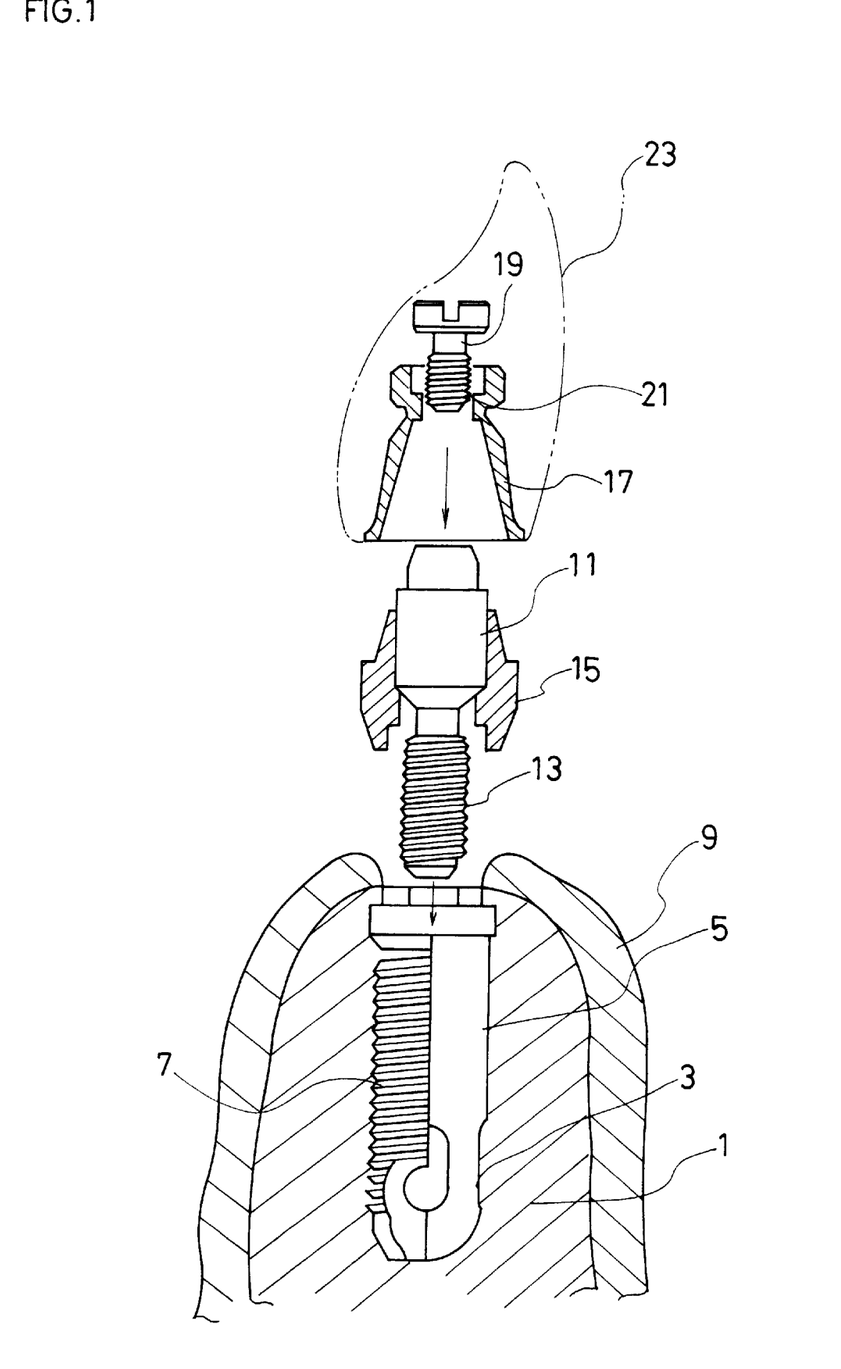
FIG. 1 is a sectional view showing a structure of an implant for "implantation" treatment in dentistry according to an embodiment of the present invention.

FIG. 1 illustrates a structure in order to fix an artificial tooth as a false tooth. An implantation hole 3 has been drilled and formed in a jaw bone 1, in which an implant 5 made of metal is implanted. The implant 5 is provided with an external thread 7 on the outer periphery thereof, and also an unillustrated internal thread on the inner periphery thereof. When the implant 5 is rotatively inserted in the implantation hole 3, the external thread 7 serves as a tapping screw so as to be engaged and in contact with the implantation hole 3. Reference numeral 9 is a gingiva (gum) 9 which covers the jaw bone 1.

For reference, the above external thread 7 may be any thread without the function of tapping screw.

The implant 5 receives an abutment screw 11 to be engaged with each other. The abutment screw 11 is provided with an external thread 13 at the bottom thereof, so that when the external thread 13 is rotatively inserted in and thus engaged with the unillustrated internal thread of the implant 5, the abutment screw 11 is engaged and in connection with the implant 5. Reference numeral 15 surrounding the outer periphery of the abutment screw 11 is an abutment. The abutment screw 11 is provided with an unillustrated internal thread on the inner periphery at the top thereof, so that the unillustrated internal thread may be engaged and in connection with a retaining screw 19 when a gold cylinder 17 is put on the outer periphery of the abutment screw 11 as well as on the abutment 15. With this regard, the retaining screw 19 is provided with an external thread 21, and when the external thread 21 is rotatively inserted in and engaged with the unillustrated internal thread of the abutment screw 11, the retaining screw is engaged and in connection with the abutment screw 11.

There is an artificial tooth 23 as illustrated by imaginary chain double-dashed line in FIG. 1. The artificial tooth 23 is fixed on the outer periphery of the gold cylinder 17 as shown in FIG. 1, thus when the retaining screw 19 is engaged with the internal thread of the abutment screw 11, the artificial tooth 23 is attached to and fixed on the abutment screw 11.

In the above mentioned structure of the artificial tooth 23 when any excessive force is applied to the artificial tooth, the retaining screw 21 will firstly receive the damage and be broken, then the abutment screw 11 will secondly receive such destructive damage. The implant 5 will remain until the above two screws 21 and 11 are broken, but may finally be broken upon receiving such an excessive force. Namely, the above described structure of the artificial tooth protects the implant 5 as much as possible against the excessive force applied to the implant 5, so that the good condition of the implant 5 as well as the structure of the artificial tooth may be maintained for a long time.

Figure 2:
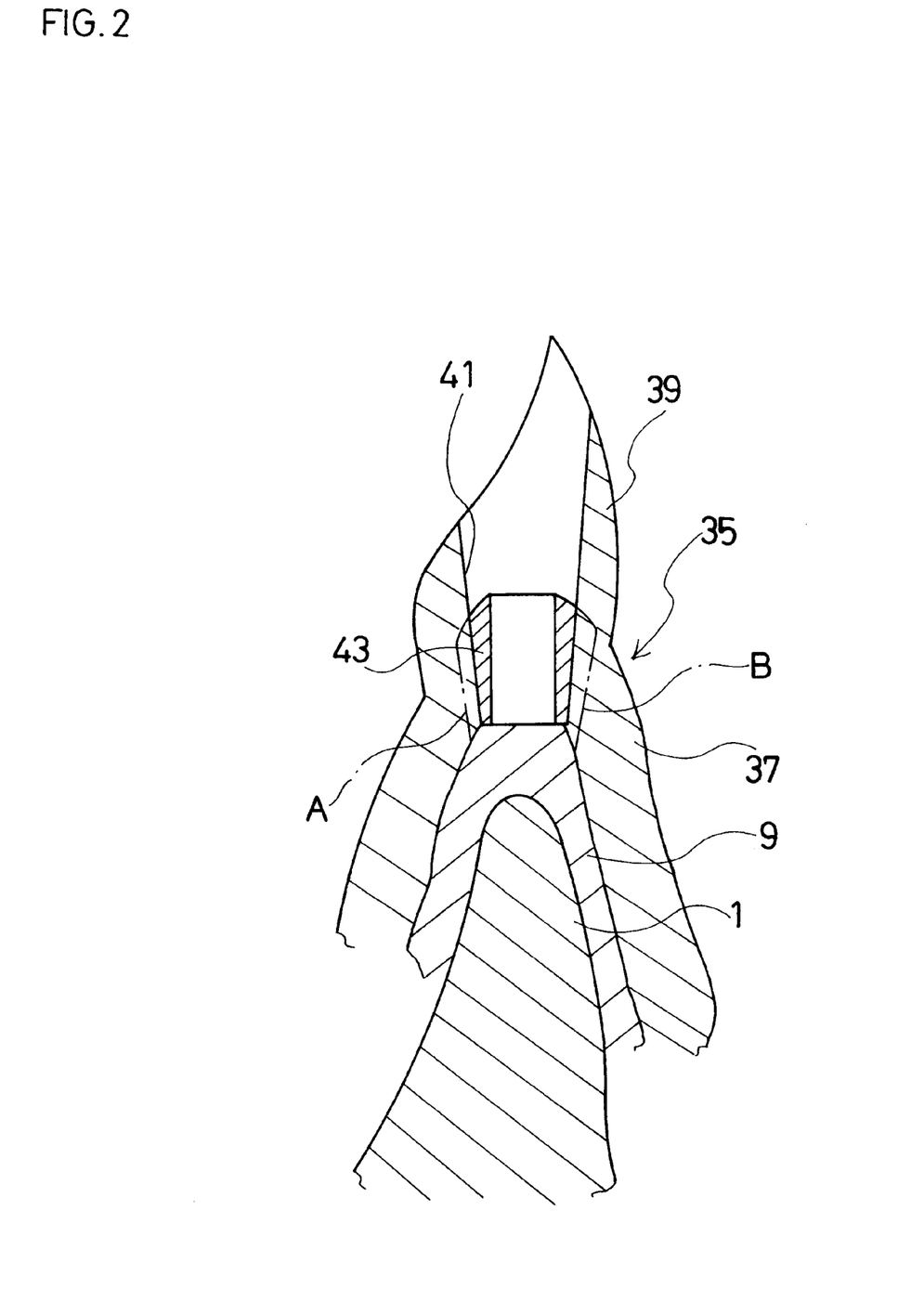
FIG. 2 is a sectional view showing a structure of a surgical stent for the implantation treatment in dentistry according to the embodiment of the present invention.

The drilling operation used to form the implantation hole 3 will now be described. Firstly, a surgical stent 35 as shown in FIG. 2 is prepared prior to the drilling operation. The surgical stent 35 comprises, for example, a main body made of plastic and an opaque agent made of barium powders, etc. The opaque agents are implanted in the predetermined positions of the main body of the surgical stent 35, so that the images of opaque agents may emerge during computed tomography. Accordingly, the surgical stent 35 is prepared after modeling of the corresponding portion from a patient. The surgical stent 35 consists of a base end 37, which covers the gingiva 9, and a tooth member 39 of which shape is identical to the shape of the artificial tooth 23, namely the shape of tooth actually fixed. The computed tomography is operated so that the surgical stent 35 is attached to the patient. Then based on the obtained image by means of computed tomography, the drilling position into the jaw bone 1 is determined, thus a hole 41 in a predetermined diameter is drilled and formed at the position corresponding to the determined position as described above.

It must be noted that, when the surgical stent 35 is attached in the mouth of the patient, the direction of implantation of the implant 5 is determined, and at the same time the type of abutment 8 used for the present artificial tooth is also determined. Consequently, as long as the implantation hole 3, which is used for implantation of the implant 5, is accurately drilled and formed, the direction of implantation as above described may accurately be determined, and thus there will be no necessity of further change of type of the abutment 8.

For reference, the drilling position into the jaw bone 1 is specified, for example, through confirmation of positions of nerves by means of computed tomography so that the drilling may be operated by avoiding the positions of nerves, or through consideration of relation of the drilling position to the other teeth.

Then a guide ring 43 having an aperture with a predetermined diameter as a guide hole is attached to and fixed on a hole 41 of the surgical stent 35. The tooth member 39 is then taken away from the surgical stent 35, and at the same time, the cutting operation is carried out along the cutting lines A and B as shown in chain lines in FIG. 3 so that the guide ring 43 and the surrounding portion thereof may remain. The surgical stent 35 in the thus obtained state is then fixed on the gingiva 9 by using the remaining teeth 36.

Figure 3:
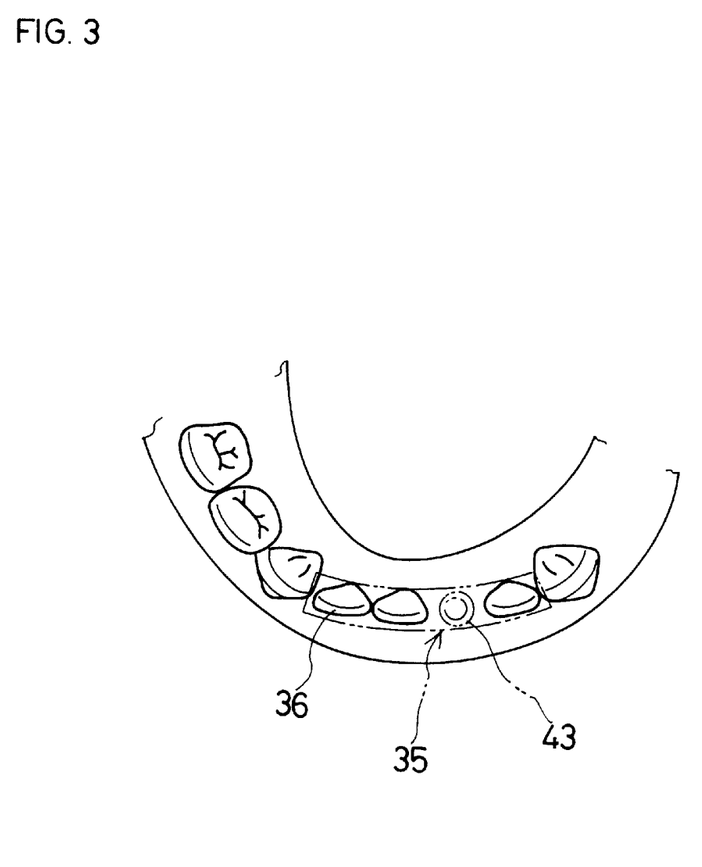
FIG. 3 is a plan view showing a structure of a surgical stent for the implantation treatment in dentistry according to the embodiment of the present invention.

If there is no remaining tooth 36, the surgical stent 35 may be fixed by using an unillustrated bite block at the alveolar ridge of the jaw bone 1.

Figure 4:
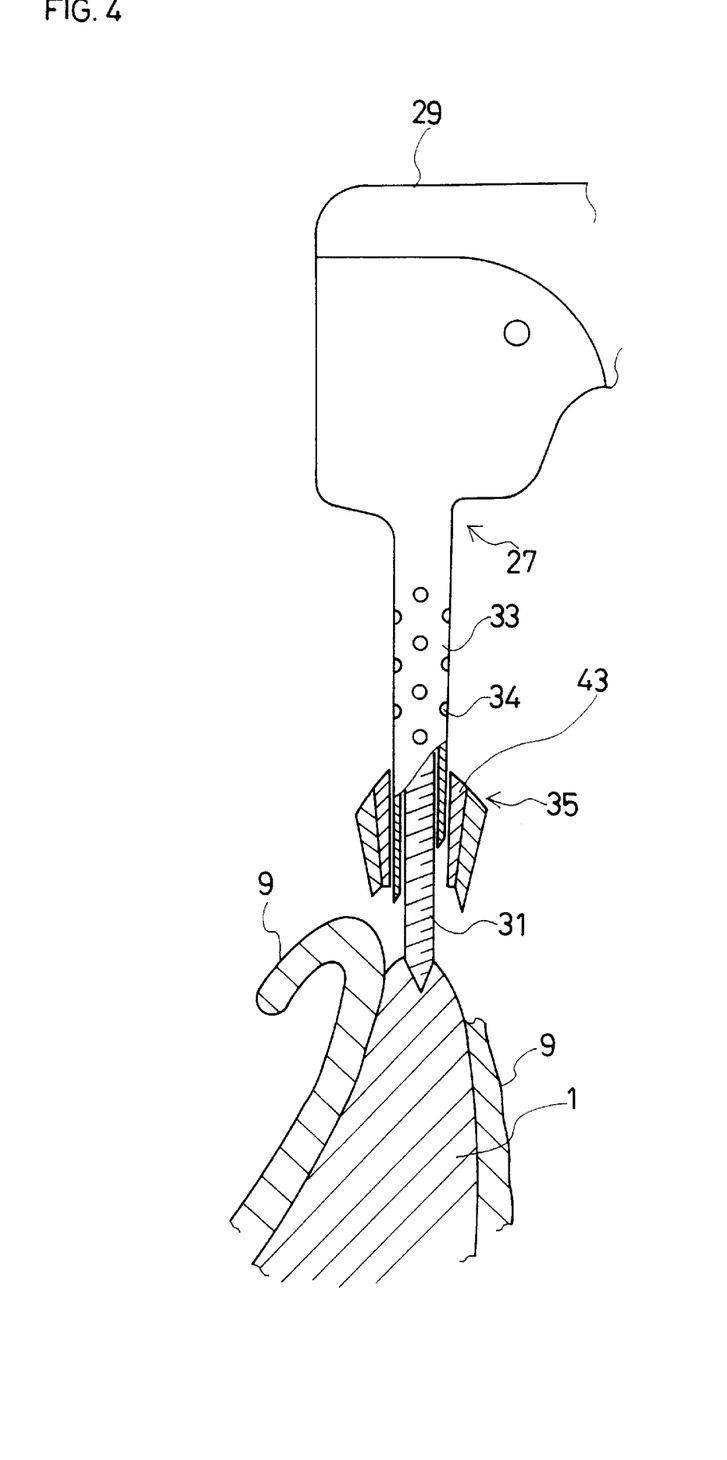
FIG. 4 is a sectional view showing a state of drilling and forming operation of an implantation hole in dentistry according to the embodiment of the present invention.

The structure of a drilling apparatus according to the embodiment of the present invention will now be described with reference to FIG. 4. As illustrated in FIG. 4, the drilling operation is carried out by using a bone drilling apparatus 27. A drilling implement 31 serves as a rotative cutting implement (drill) and is provided at the top end of the drilling device 29. A guide member 33 surrounds the drilling implement 31 without having any contact point therebetween. The top of the guide member 33 is cut away in an oblique direction as seen by the sectional view (see FIG. 4), and the tubular portion of the guide member 33 has a plurality of holes which serves as a plurality of water fillers 34.

In addition, since the top of the guide member 33 is cut away, the water may also be filled through the top of the guide member 33.

The gingiva 9 has been partially cut to form a curled shape, so that the jaw bone 1 at the cut position may be exposed. As discussed above, the surgical stent 35 has been attached to and fixed on the upper portion of the exposed jaw bone 1.

The diameter of aperture of the guide ring 43 substantially corresponds to the diameter of the outer periphery of the guide member 33. Consequently, when the guide member 33 is inserted in the guide ring 43, the engagement with each other allows almost no play therebetween. Accordingly, when the drilling operation is carried out, the guide member 33 is inserted in the guide ring 43 in order to fix the guide ring 43 at any position in order to inhibit the movement of the guide ring 43 in the radial direction. Thus, drilling is operated into the jaw bone 1.

During the drilling operation, the water is filled, and the filled water is introduced via the water fillers 34 to the space between the guide member 33 and the drilling implement 31 in order to remove heat as well as the shavings during drilling operation.

In addition, since the top end of the guide member 33 is obliquely cut away as illustrated in FIG. 4, the water is filled through such a cut away portion in order to remove the shavings.

The guide ring 43 and the guide member 33 are preferably made of, for example, stainless steel or titanium, but it is of course clear that the material is not limited to stainless steel or titanium. Further, the size of each part may arbitrarily determined.

Figure 5:
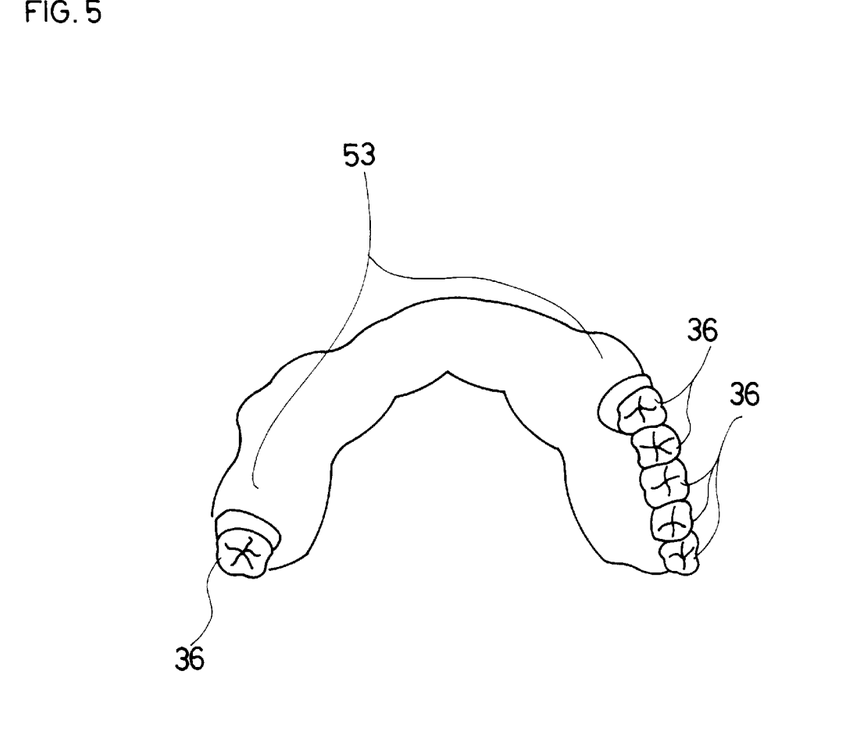
FIG. 5 is a view according to the embodiment of the present invention showing a state inside the mouth of patient to whom the implantation treatment is operated.

The drilling operation according to the embodiment of the present invention, that is especially carried out for implantation of the implant 5, will now be described in detail with reference to FIGS. 5 through 13. FIG. 5 illustrates an example of the mouth of the patient on the side of the upper jaw subject to the implantation treatment. In this example of FIG. 5, there are five remaining teeth 36, one of which is positioned on the left, and the rest is positioned on the right, with a portion having no tooth in between. The artificial tooth shall be fixed on the portion having no tooth, which is illustrated as reference numeral 53 in FIG. 5, by means of implantation treatment according to the present invention.

Figure 6A:
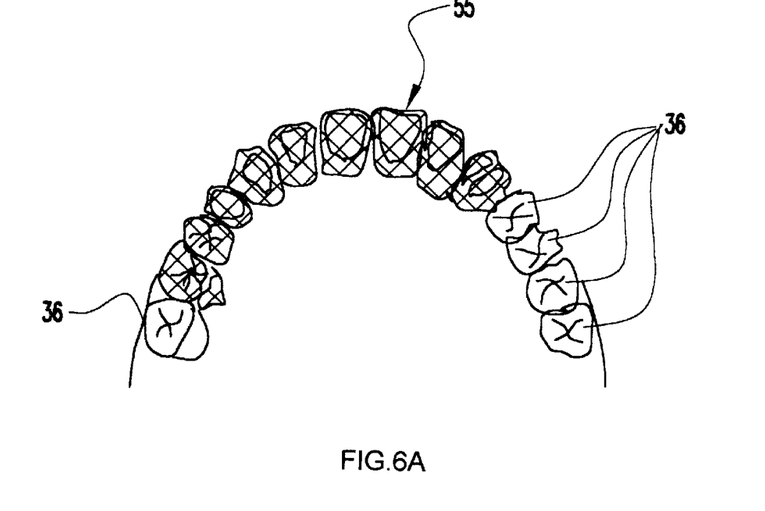
FIG. 6(a) is a view according to the embodiment of the present invention showing a state of a future expectation model made of wax prepared through modeling.
Figure 6B:
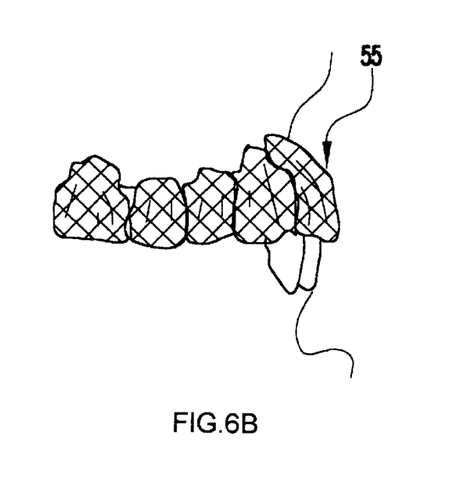
FIG. 6(b) is a view according to the embodiment of the present invention showing a state of a future expectation model made of wax prepared through modeling.
Figure 6C:
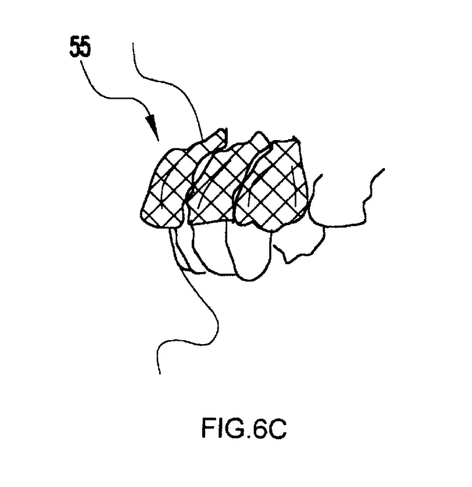
FIG. 6(c) is a view according to the embodiment of the present invention showing a state of a future expectation model made of wax prepared through modeling.
Figure 7:
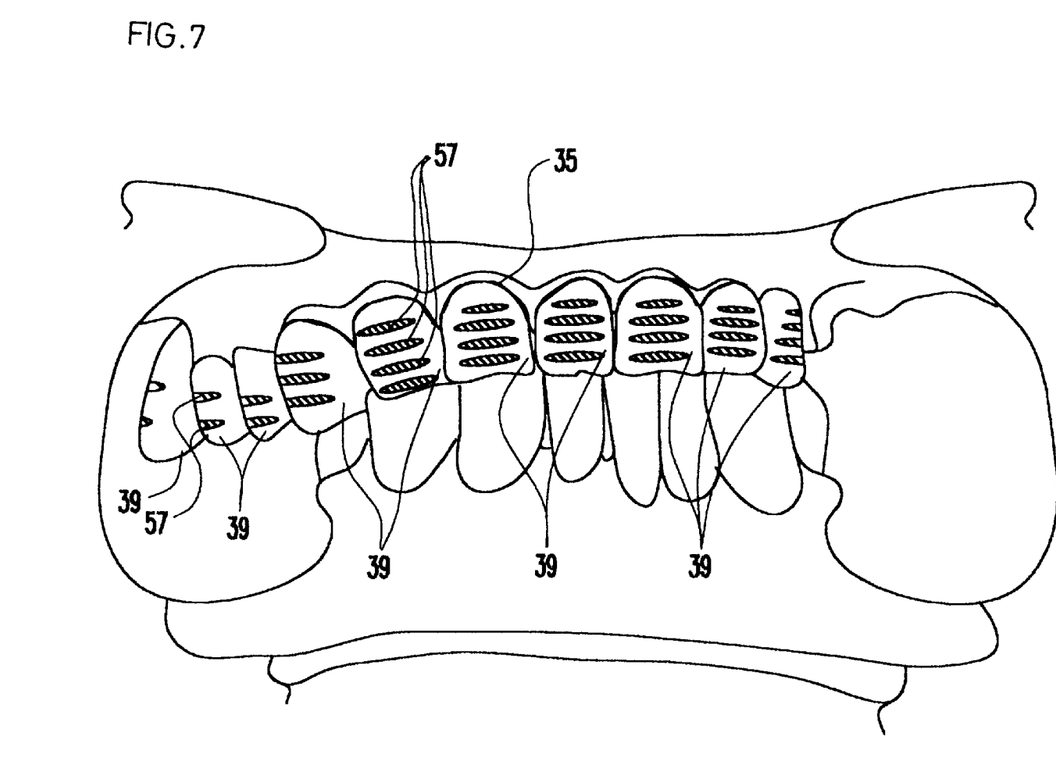
FIG. 7 is a view according to the embodiment of the present invention showing a state in which a surgical stent is attached in order to carry out computed tomography.
Figure 8:
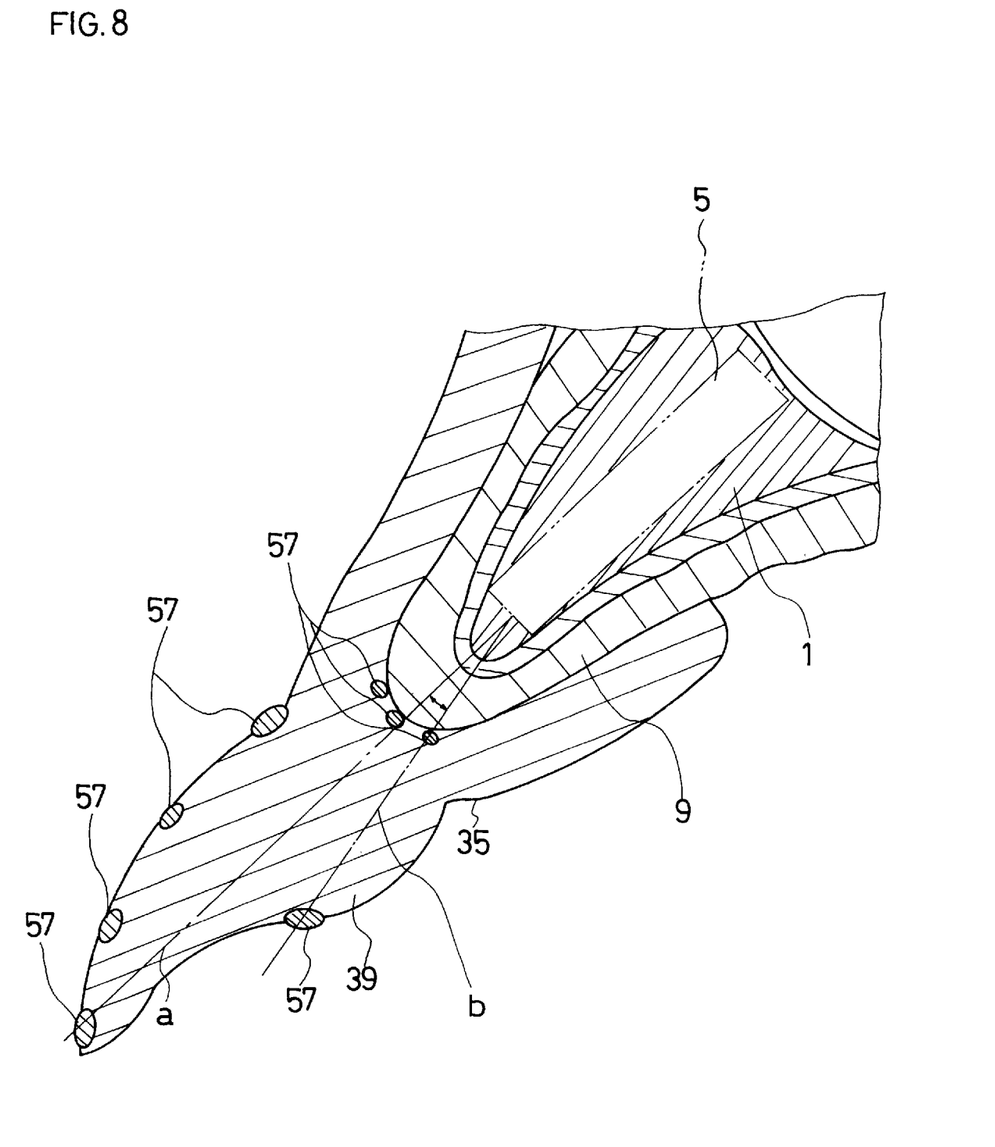
FIG. 8 is a simulate view according to the embodiment of the present invention showing a simulated state in which a position and a direction of drilling is determined based on an image obtained by computed tomography.
Figure 9:
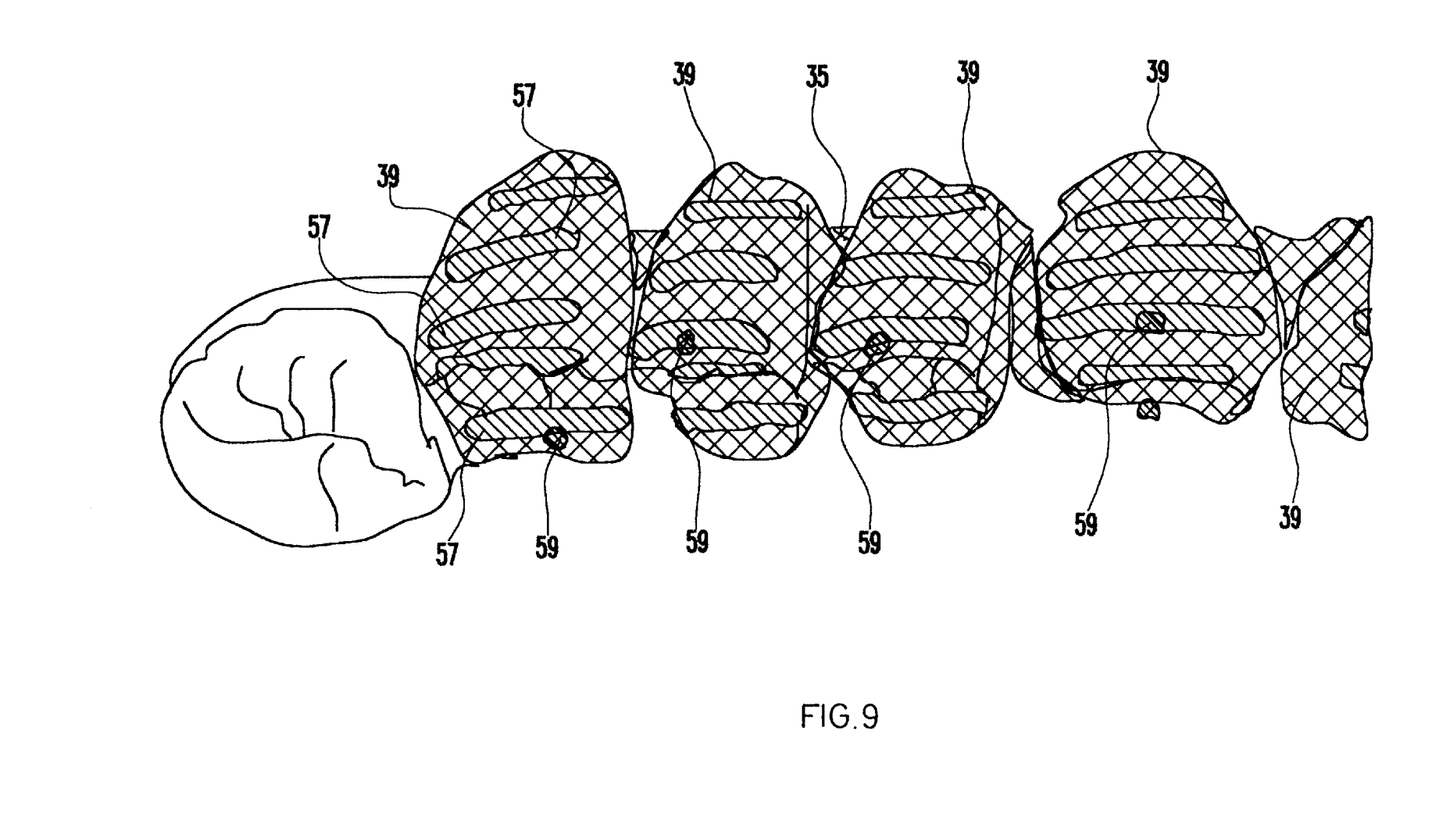
FIG. 9 is a view according to the embodiment of the present invention showing a state in which markings are made on a surgical stent based on an image obtained by computed tomography.

In the drilling operation especially carried out for implantation treatment, a future expectation model 55, which is shown as a faintly darkened portion in FIGS. 6(a) (b) and (c), are firstly prepared. The preparation of teeth of the future expectation model 55 made of wax is carried out by modeling from the patient, taking account of occlusion of the upper and lower teeth. The surgical stent 35 made of plastic, shown as a faintly darkened portion in FIG. 7, is then prepared based on the future expectation model 55. The surgical stent 35 comprises a plurality of teeth 39, and X-ray opaque agent 57 is implanted in each tooth 39 so as to form a plurality of lines (The portions darkened by oblique lines in FIG. 7 show the portions in which the X-ray opaque agents 57 are implanted). The X-ray opaque agent 57 may be implanted at positions such as the front of the teeth 39, the back of the teeth 39, or the inner periphery of the surgical stent 35 on the side of the jaw bone 1, as illustrated in FIG. 8. Since the X-ray opaque agents 57 are implanted in lines, such portions having the X-ray opaque agents 57 emerge as the opaque portions during computed tomography. Thus the positions and directions of drilling operation are determined based on the emerging opaque portions.

The thus prepared surgical stent 35 is fixed on the upper jaw of the patient (FIG. 7 shows a state that the surgical stent 35 is fixed on the upper jaw of the patient). The computed tomography is carried out in this state. The computed tomography enables a dentist or an operator to check the states of the maxilla or the nerves of the patient, thus the positions and directions of drilling are determined by observing the obtained image.

For the purpose of easy understanding, the above description will repeatedly be made with reference to the FIG. 8. FIG. 8 is a simulation view according to the present invention. As described above, the surgical stent 35 has the X-ray opaque agents 57 implanted in lines. When the computed tomography is carried out in this state, the dentist or the operator may confirm the X-ray opaque agents 57, the jaw bone 1, etc., as illustrated in FIG. 8. Then the positions and directions of drilling are determined by observing the image obtained by computed tomography, taking account of position of the jaw bone 1 or other conditions of the patient. In the case of simulation in FIG. 8 relating one tooth, the most preferable position and direction of drilling are determined as a line "a" in FIG. 8. Accordingly, the markings 59 are made at the positions where the line "a" can be specified, like the case of FIG. 9. Then the drilling is operated along the line "a" which is formed by connecting the markings 59. The retaining screw 19 as shown in FIG. 1 is screwed in the direction as illustrated by a line "b" in FIG. 8, so that the surface of the retaining screw 19 may not be seen from the front of the patient.

Figure 10:
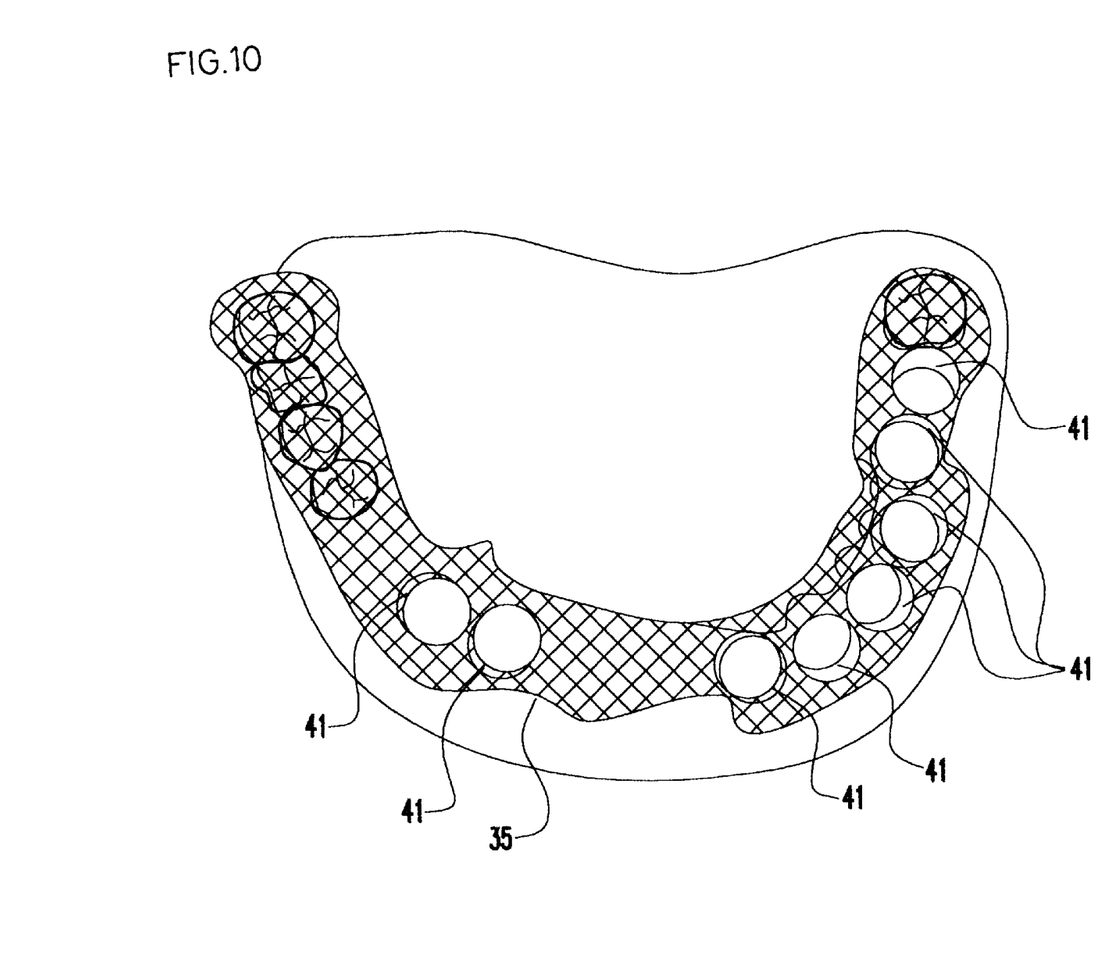
FIG. 10 is a view according to the embodiment of the present invention showing a state of a surgical stent that predetermined drillings are operated and excess portions are cut.
Figure 11:
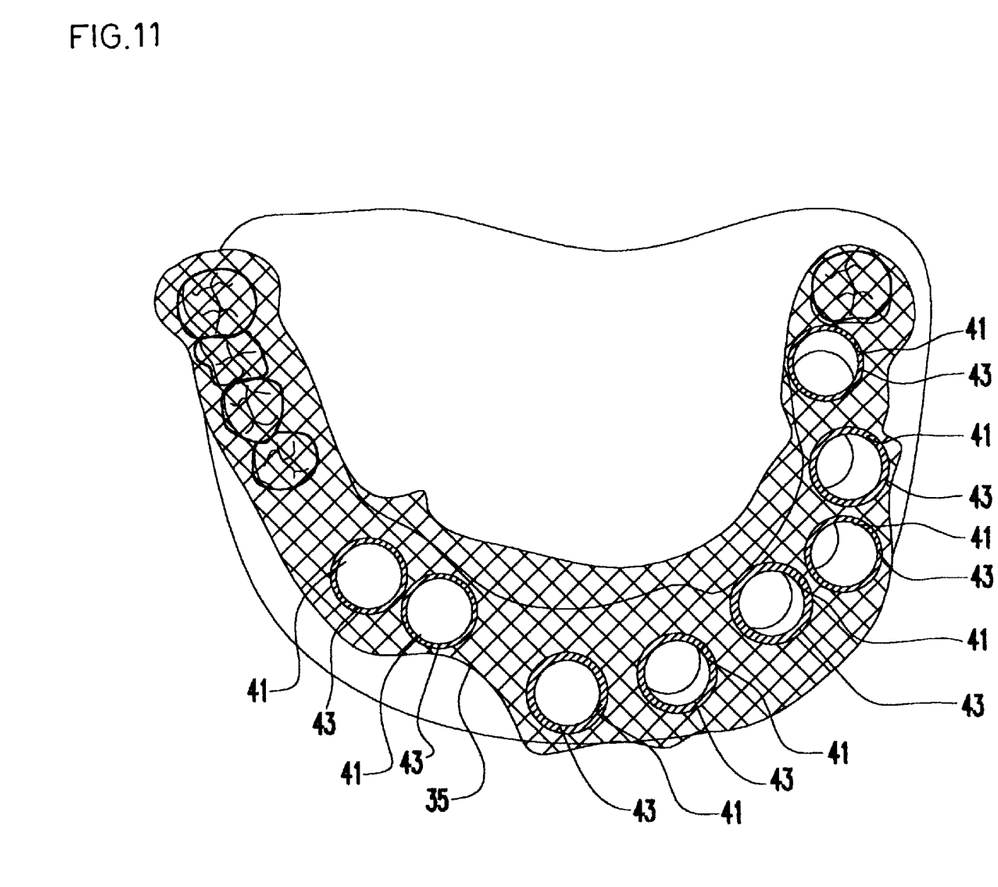
FIG. 11 is a view according to the embodiment of the present invention showing a state in which guide rings are fixed inside holes of a surgical stent as shown in FIG. 10.
Figure 12:
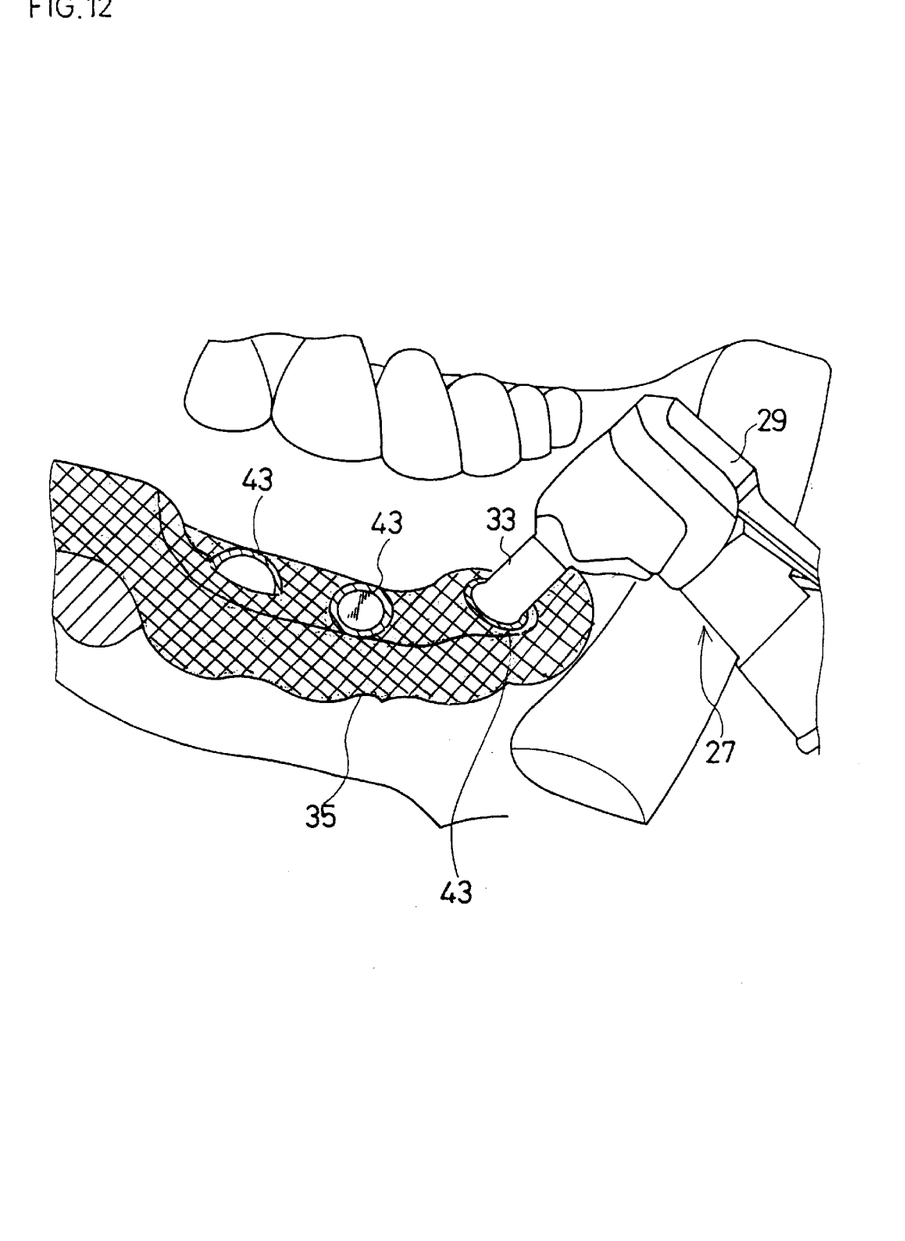
FIG. 12 is a view according to the embodiment of the present invention showing a drilling operation by a drilling apparatus into a surgical stent with the guide ring fixed on a predetermined position inside the mouth of a patient.
Figure 13:
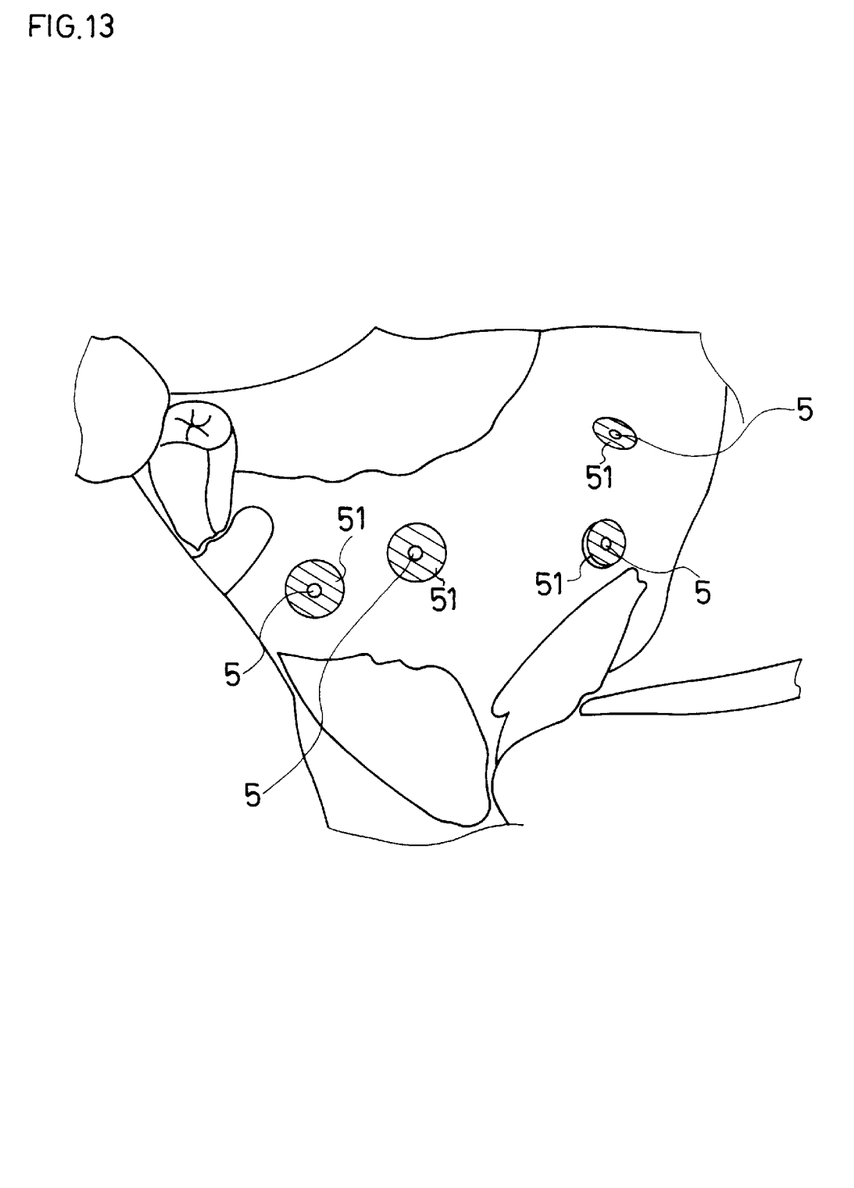
FIG. 13 is a view according to the embodiment of the present invention showing a implants that have been implanted after drilling by the drilling apparatus.

After drilling along the line "a", the surgical stent 35 is removed as illustrated in FIG. 10, and the predetermined drilling operation (the drilling operation along the line "a" as above described) is carried out in order to form the plurality of holes 41. At the same time, the unnecessary parts are cut away, thus the state as shown in FIG. 10 is obtained. Then the guide rings 43 are placed inside the holes 41 as shown in FIG. 11. After that, the surgical stent 35 is again fixed inside the mouth of the patient, so that the bone drilling apparatus 27 according to the present invention may operate the drilling direct into the maxilla, as illustrated in FIG. 12. The implants 5 are then implanted in the drilled holes 41, and the holes 41 are then covered by caps 51 for any fixed curing period, as illustrated in FIG. 13. After expiration of the curing period, the caps 51 are removed from the holes 41, to which the teeth 23 are fixed according to the structure as illustrated in FIG. 1.

The present invention has the following advantageous points.

Firstly, there is a guide ring 43 in which the guide member 33 is inserted, so that the position of the guide member 33 is fixed and thus the guide member 33 is unable to move in the radial direction. Therefore it is possible to accurately drill and form the predetermined implantation hole 3 into the jaw bone 1. Such a structure will require neither the skilled operation nor the long time for operation, thus enabling an operator to drill and form the implantation hole 3 at the accurate position. Consequently, the implantation treatment itself may become a facile operation.

Since the implantation hole 3 can be accurately drilled and formed, the need for further operations to amend the position of the hole are no longer required. Thus the efficiency of operation may improve.

In relation to the water filling, there is a plurality of water fillers 34, and in addition, the top end of the guide member 33 is obliquely cut away. Therefore sufficient water may be filled during operation.

When the length of the guide member 33 is determined, the length of the drilling implement 31 projecting from the top end of the guide member 33 is automatically fixed. Therefore the drilling operation may be carried out at the unified length according to the determined length of the guide member 33, thus the operation is facilited.

In addition, the present invention will not damage the surgical stent 35 during drilling, and problems resulting from damage to the stent will not occur.

The present invention is not limited to the embodiment as described above.

Although the embodiment refers to the case of implantation treatment in dentistry, the present invention can be applied to the drilling operations into any other bones, for example, into the femur.

It is possible to arbitrarily determined the diameters, shapes and sizes of the guide member and the guide ring.

In one embodiment of the present invention, the guide member 33 is provided separate from the drilling implement 31. However, it is also possible to provide an integral guide member, for example, by enlarging the base end of the drilling implement 31 in order to serve as the guide member.

In addition, in one embodiment of one present invention, the guide ring is provided, and the guide hole having a predetermined diameter is formed in the guide ring. However, it is also possible to use the hole on the side of the surgical stent as the guide hole, by preparing such a hole at a predetermined diameter.

What is claimed is:

1. An apparatus for jaw bone drilling in dentistry comprising:

a support member for attachment to a jaw bone be drilled, said support member comprising a guide hole having a predetermined aperture diameter;

a drilling device provided with a rotative cutting implement;

a guide member provided on an outer periphery of said rotative cutting implement with a space therebetween, wherein a diameter of the outer periphery of said guide member substantially corresponds to said predetermined aperture diameter of said guide hole; and a plurality of water fillers formed on said guide member in order to introduce water inside said guide member.

2. An apparatus for jaw bone drilling in dentistry comprising:

a support member for attachment to a jaw bone be drilled, said support member comprising a guide hole having a predetermined aperture diameter;

a drilling device provided with a rotative cutting implement; and a guide member provided on an outer periphery of said rotative cutting implement with a space therebetween, wherein a diameter of the outer periphery of said guide member substantially corresponds to said predetermined aperture diameter of said guide hole, wherein a top end of said guide member is obliquely cut away so that water may be filled from said top end.

3. An apparatus for jaw bone drilling in dentistry comprising:
- a surgical stent, to be attached to a position corresponding to implantation position on a jaw bone, and provided with at least one guide hole having a predetermined aperture diameter;
- a drilling device provided with a rotative cutting implement;
- a guide member provided on an outer periphery of said rotative cutting implement having a space therebetween, wherein a diameter of the outer periphery of said guide member substantially corresponds to said predetermined aperture diameter of said guide hole; and
- a plurality of water fillers formed on said guide member in order to introduce water inside said guide member.

4. An apparatus for jaw bone drilling in dentistry comprising:
- a surgical stent, to be attached to a position corresponding to implantation position on a jaw bone, and provided with at least one guide hole having a predetermined aperture diameter;
- a drilling device provided with a rotative cutting implement; and
- a guide member provided on an outer periphery of said rotative cutting implement having a space therebetween, wherein a diameter of the outer periphery of said guide member substantially corresponds to said predetermined aperture diameter of said guide hole, wherein a top end of said guide member is obliquely cut away so that water may be filled from said top end.

5. A method of jaw bone drilling in dentistry comprising the steps of:
- attaching a support member provided with a guide hole having a predetermined aperture diameter to the side of a jaw bone;
- preparing a drilling device provided with a rotative cutting implement to be rotated, wherein a guide member is provided on the outer periphery of said rotative cutting implement and having a space therebetween, and wherein a diameter of the outer periphery of said guide member substantially corresponds to said predetermined aperture diameter of said guide hole; and
- drilling with said rotative cutting implement when said guide member is inserted in said guide hole.

6. The method of jaw bone drilling in dentistry as claimed in claim 5, further comprising the step of:
- providing a guide ring, having a predetermined aperture diameter, on said guide hole.

7. A method of jaw bone drilling in dentistry comprising the steps of:
- attaching a surgical stent, comprising at least one guide hole having a predetermined aperture diameter, to a position corresponding to implantation position on a jaw bone;
- preparing a drilling device provided with a rotative cutting implement and a guide member provided on the outer periphery of said rotative cutting implement, wherein a diameter of the outer periphery of said guide member substantially corresponds to said predetermined aperture diameter of said guide hole; and
- drilling with said rotative cutting implement when said guide member is inserted in said guide hole.

8. The method of jaw bone drilling in dentistry as claimed in claim 7, further comprising the step of:
- providing a guide ring, having a predetermined aperture diameter, on said guide hole.

9. An apparatus for jaw bone drilling in dentistry comprising:
- a support member for attachment to a jaw bone be drilled, said support member comprising a guide hole having a predetermined aperture diameter;
- a drilling device provided with a rotative cutting implement;
- a guide member provided on an outer periphery of said rotative cutting implement with a space therebetween, wherein a diameter of the outer periphery of said guide member substantially corresponds to said predetermined aperture diameter of said guide hole;
- a guide ring provided on said guide hole, and a diameter of the outer periphery of said guide member of said drilling device substantially corresponds to a diameter of said aperture of said guide ring; and
- a plurality of water fillers formed on said guide member in order to introduce water into said guide member.

10. An apparatus for jaw bone drilling in dentistry comprising:
- a support member for attachment to a jaw bone be drilled, said support member comprising a guide hole having a predetermined aperture diameter;
- a drilling device provided with a rotative cutting implement;
- a guide member provided on an outer periphery of said rotative cutting implement with a space therebetween, wherein a diameter of the outer periphery of said guide member substantially corresponds to said predetermined aperture diameter of said guide hole; and
- a guide ring provided on said guide hole, and a diameter of the outer periphery of said guide member of said drilling device substantially corresponds to a diameter of said aperture of said guide ring, wherein a top end of said guide member is obliquely cut away so that water may be filled from said top end.

11. An apparatus for jaw bone drilling in dentistry comprising:
- a surgical stent, to be attached to a position corresponding to implantation position on a jaw bone, and provided with at least one guide hole having a predetermined aperture diameter;
- a drilling device provided with a rotative cutting implement;
- a guide member provided on an outer periphery of said rotative cutting implement having a space therebetween, wherein a diameter of the outer periphery of said guide member substantially corresponds to said predetermined aperture diameter of said guide hole;
- a guide ring provided on said guide hole of said surgical stent, wherein a diameter of the outer periphery of said guide member of said drilling device substantially corresponds to a diameter of said aperture of said guide ring; and
- a plurality of water fillers formed on said guide member in order to introduce water into said guide member.

12. An apparatus for jaw bone drilling in dentistry comprising:

a surgical stent, to be attached to a position corresponding to implantation position on a jaw bone, and provided with at least one guide hole having a predetermined aperture diameter;

a drilling device provided with a rotative cutting implement;

a guide member provided on an outer periphery of said rotative cutting implement having a space therebetween, wherein a diameter of the outer periphery of said guide member substantially corresponds to said predetermined aperture diameter of said guide hole; and a guide ring provided on said guide hole of said surgical stent, wherein a diameter of the outer periphery of said guide member of said drilling device substantially corresponds to a diameter of said aperture of said guide ring, wherein a top end of said guide member is obliquely cut away so that water may be filled from said top end.

13. An apparatus for preparing and drilling an implant hole in a jaw bone, comprising:

a surgical stent for positioning over a drilling site on a jaw bone;

a guide ring positioned within said surgical stent, said guide ring comprising a cylindrical inner diameter; and a drilling device, said drilling device comprising:

a hollow cylindrical guide member sized to slide vertically within said cylindrical inner diameter of said guide ring;

a plurality of water introduction holes in said hollow cylindrical guide member; and a surgical drill contained within said hollow cylindrical guide member having a space between said hollow cylindrical guide member and said drill for allowing water from said plurality of water introduction holes to circulate within said space to cool said drill and flush away jaw bone shavings created by said surgical drill.

* * * * *